United States Patent [19]
Ward et al.

[11] Patent Number: 5,872,132
[45] Date of Patent: Feb. 16, 1999

[54] FORM OF PAROXETINE HYDROCHLORIDE ANHYDRATE

[75] Inventors: Neal Ward, East Sussex; Victor Witold Jacewicz, Kent, both of England

[73] Assignee: SmithKline Beecham Corporation, Philadelphia, Pa.

[21] Appl. No.: 733,874

[22] Filed: Oct. 18, 1996

Related U.S. Application Data

[63] Continuation of Ser. No. 444,661, May 19, 1995, abandoned.

[30] Foreign Application Priority Data

Feb. 6, 1995 [GB] United Kingdom ............... 9502297
Feb. 17, 1995 [GB] United Kingdom ............... 9503112

[51] Int. Cl.$^6$ ............ A61K 31/445; C07D 405/12
[52] U.S. Cl. ............................. 514/321; 546/197
[58] Field of Search ................ 514/321; 546/197

[56] References Cited

U.S. PATENT DOCUMENTS

| | | | |
|---|---|---|---|
| 3,912,743 | 10/1975 | Christensen | 546/197 |
| 4,007,196 | 2/1977 | Christensen | 546/197 |
| 4,721,723 | 1/1988 | Barnes et al. | 514/321 |
| 4,745,122 | 5/1988 | Lassen | 514/321 |
| 5,672,612 | 9/1997 | Ronsen et al. | 514/338 |

FOREIGN PATENT DOCUMENTS

| | | |
|---|---|---|
| 190496 | 8/1986 | European Pat. Off. . |
| 374674 | 6/1989 | European Pat. Off. . |

OTHER PUBLICATIONS

Fox et al. "Physics and chemistrh of the organic solid state" Inter. Sci. pp. 180–182, 369–370, 398–400, 1963.

Buxton et al., International Journal of Pharmaceutics, 42: pp. 135–143 (1988).

Buxton et al. "Solid–State Forms of Paroxetine Hydrochloride", Publication presented at meeting of Joint Pharm. Analysis Group in London on Oct. 8, 1987.

Lynch et al. "Infrared spectroscopic studies on the solid state forms of paroxetine hydrochloride" Analytical proceedings, vol. 25, pp. 305–306, 1988.

Henndy, N.B. "Crystalline and noncrystalline solids" Plenum Press, vol.3, pp. 89–90, 1977.

Evans R.C. "An introduction to crystal chemistry" Cambridge Univ. Press, pp. 393–397, 1964.

Wennogle, et al., Life Sciences, vol. 36, pp. 1541–1550 (1985).

Fuller, et al., Neuropharmacology, vol. 23, pp. 539–544 (1984).

Chung, et al., Communications in Psychopharmacology, vol. 4, pp. 161–167 (1980).

Lund, et al., Acta Pharmacology et Toxicology, vol. 44, pp. 289–295 (1979).

Middlemiss, Naunyn–Schmiedeberg's Arch Pharmacology, 327:18–22.

Laursen, et al., Acta psychiatr. scand, 71:249–255 (1985).

*Primary Examiner*—Ceila Chang
*Attorney, Agent, or Firm*—Edward T. Lentz

[57] ABSTRACT

"Paroxetine hydrochloride (I) anhydrate

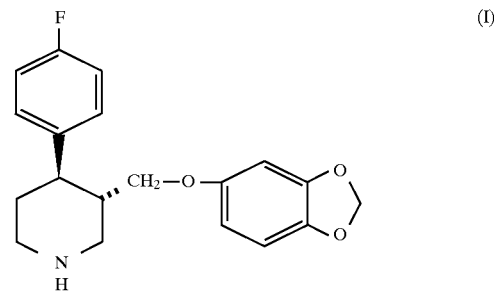

(I)

free of bound propan-2-ol, and various forms thereof, are useful in the treatment of depression and other disorders for which administration of selective serotonin reuptake inhibitors are indicated."

2 Claims, 12 Drawing Sheets

Solid state C13 NMR spectrum
paroxetine hydrochloride anhydrate
polymorph A

Solid state C13 NMR spectrum
paroxetine hydrochloride anhydrate
polymorph B

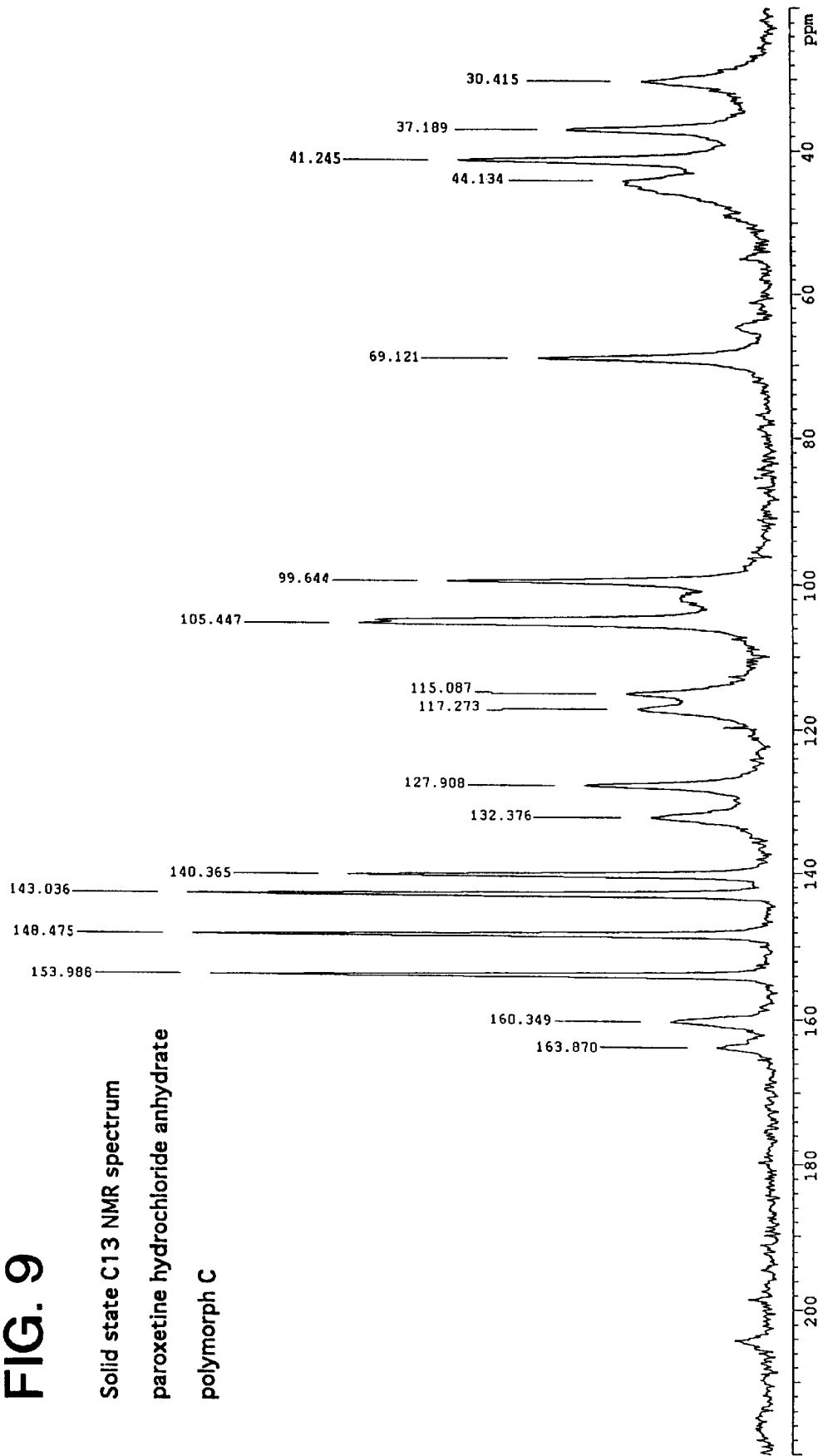

FORM OF PAROXETINE HYDROCHLORIDE ANHYDRATE

This is a filewrapper continuation of application Ser. No. 08/444,661, filed May 19, 1995, now abandoned.

FIELD OF THE INVENTION

The present invention relates to novel compounds, to processes for preparing them and to their use in treating medical disorders.

BACKGROUND OF THE INVENTION

U.S. Pat. No. 4,721,723 (Beecham Group plc) describes paroxetine hydrochloride hemi-hydrate and its use in treating certain medical disorders. Example 8 in U.S. Pat. No. 4,721,723 describes the preparation of paroxetine hydrochloride anhydrate as platelets, by crystallization from a water-containing solvent. This material is hereinafter referred to as Form Z. Subsequent repetition of the preparation described in Example 8 has failed to yield any type of paroxetine hydrochloride anhydrate, and there is no clear teaching elsewhere in the document of any alternative route or modification to the process which would generate the anhydrate.

Paroxetine hydrochloride anhydrate is also purported to be disclosed in the International Journal of Pharmaceutics 42, (1988) 135 to 143, published by Elsevier. The anhydrate is said to be produced by crystallizing paroxetine hydrochloride from anhydrous propan-2-ol. Subsequent repetition of this process has resulted in a propan-2-ol solvate of paroxetine hydrochloride. That is to say that there is bound propan-2-ol in the product. This bound propan-2-ol cannot be removed by conventional drying techniques such as vacuum oven drying.

Paroxetine hydrochloride anhydrate substantially free of bound propan-2-ol, has not been described in the literature, nor has any method been disclosed which would yield such a product as an inevitable result. A method for preparing paroxetine hydrochloride anhydrate substantially free of bound propan-2-ol has now been found. Furthermore, surprisingly, four new forms of paroxetine hydrochloride anhydrate have been found as have processes for their preparation. These forms are hereinafter referred to as A, B, C and D respectively.

SUMMARY OF THE INVENTION

Accordingly, the present invention provides paroxetine hydrochloride anhydrate substantially free of bound propan-2-ol.

The present invention also provides paroxetine hydrochloride anhydrate substantially free of bound organic solvent.

The present invention also provides paroxetine hydrochloride anhydrate substantially free of propan-2-ol with the proviso that it is other than Form Z.

Substantially free of bound organic solvent is to be interpreted to be less than the amount of propan-2-ol which would remain solvated, i.e., bound, within the crystal lattice of the product under conventional vacuum oven drying conditions.

The present invention also provides paroxetine hydrochloride solvates other than the propan-2-ol solvate as precursors in the preparation of paroxetine hydrochloride anhydrate substantially free of bound organic solvent. Examples of such solvates include solvates from alcohols (other than propan-2-ol) such as propan-1-ol and ethanol; solvates from organic acids such as acetic acid; solvates from organic bases such as pyridine; solvates from nitriles such as acetonitrile; solvates from ketones such as acetone and butanone; solvates from ethers such as tetrahydrofuran and solvates from chlorinated hydrocarbons such as chloroform and solvates of hydrocarbons such as toluene.

BRIEF DESCRIPTION OF THE FIGURES

FIG. 9 is a solid state $^{13}$C-NMR spectra for Form C.

DETAILED DESCRIPTION OF THE INVENTION

Preferably, paroxetine hydrochloride anhydrate substantially free of bound propan-2-ol is provided in substantially pure form. Suitably, paroxetine hydrochloride anhydrate substantially free of bound propan-2-ol is provided with a purity of the paroxetine hydrochloride anhydrate of greater than 50%, preferably greater than 60%, more preferably greater than 70%, yet more preferably greater than 80% and even more preferably greater than 90%. Most preferably the paroxetine hydrochloride anhydrate substantially free of bound propan-2-ol is greater than 95% pure.

It should be understood that the present invention comprising paroxetine hydrochloride anhydrate substantially free of bound propan-2-ol may contain unbound water that is to say water which is other than water of crystallization.

Typically the amount of bound organic solvent on a weight for weight basis would be less than 2.0%, preferably less than 1.8%, more preferably less than 1.5%, even more preferably less than 1.0%, yet more preferably less than 0.5% and most preferably less than 0.1%.

Generally, all percentages indicated herein are on a weight for weight basis unless otherwise stated.

Preferred forms of paroxetine hydrochloride anhydrate substantially free of bound propan-2-ol or substantially free of bound organic solvent include:
i) paroxetine hydrochloride anhydrate in Form A; (as hereinafter defined)
ii) paroxetine hydrochloride anhydrate in Form B; (as hereinafter defined)
iii) paroxetine hydrochloride anhydrate in Form C; (as hereinafter defined)
iv) paroxetine hydrochloride anhydrate in Form D; (as hereinafter defined)

The forms of paroxetine hydrochloride anhydrate may be distinguished from each other and the material formed as a result of carrying out the procedures mentioned in U.S. Pat. No. 4,721,723 and the International Journal of Pharmaceutics 42, (1988), 135 to 143, by crystalline shape, by solvent analysis or by techniques such as IR, melting point, X-ray diffraction, NMR, DSC, microscopy and any other analytical techniques which differentiate one form from another.

For example, Form A substantially free of solvent may be distinguished over Form Z by its crystalline shape (Form A: needles; Form Z: platelets) and is also characterized by the following analytical data. Form A has a melting point of about 123°–125° C. when obtained in similar purity to the material described in Example 1 which may be determined by conventional methods such as HPLC and significant IR bands (FIG. 1) at about 513, 538, 571, 592, 613, 665, 722, 761, 783, 806, 818, 839, 888, 906, 924, 947, 966, 982, 1006, 1034, 1068, 1091, 1134, 1194, 1221, 1248, 1286, 1340, 1387, 1493, 1513, 1562, 1604, 3402, 3631 $cm^{-1}$.

Figure 4:
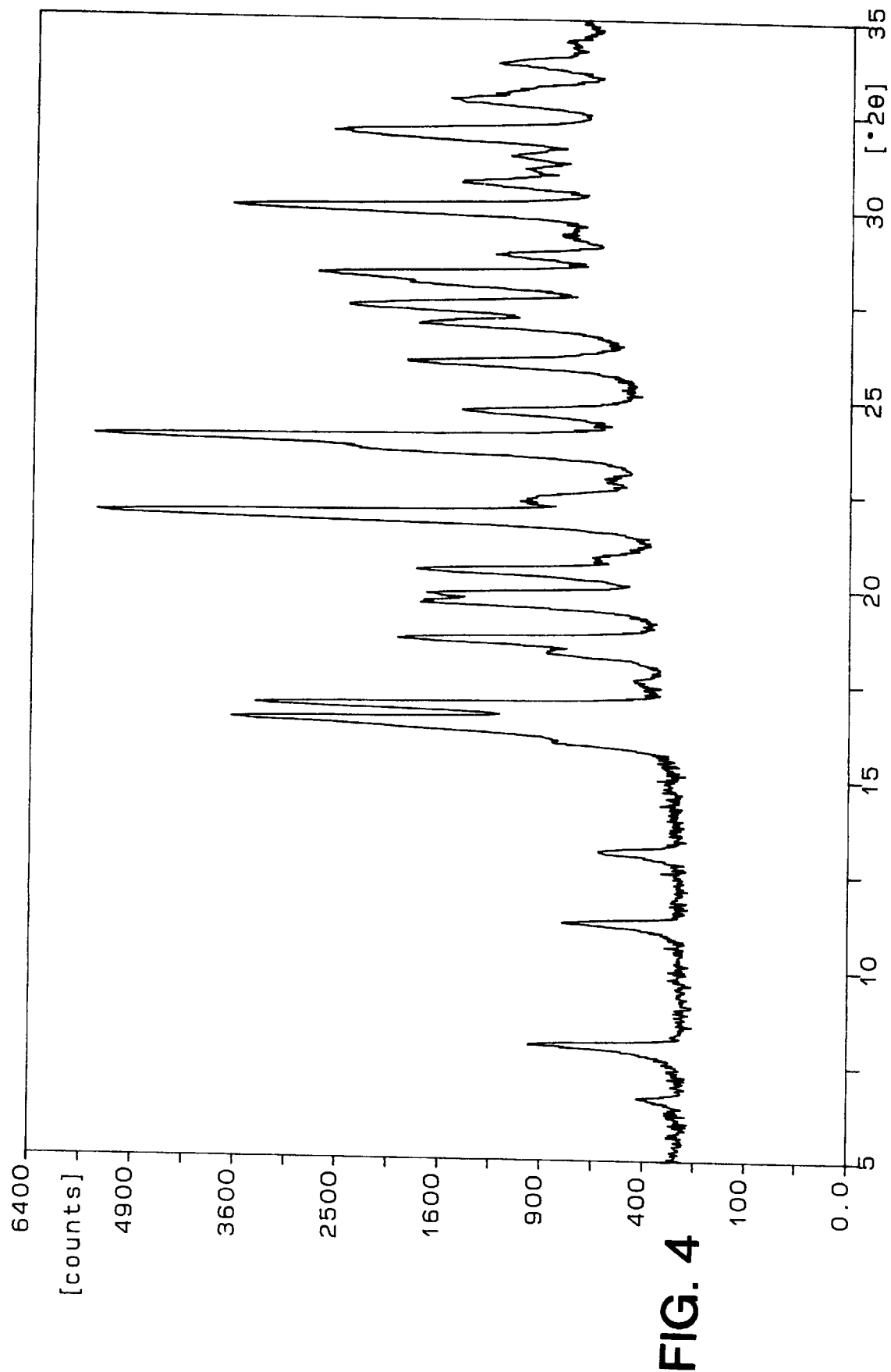
FIG. 4 is an x-ray diffractogram for Form A.

The DSC exotherm, measured at 10° C. per minute shows a maximum at about 126° C. using an open pan and a maximum at about 121° C. using a closed pan. Form A also has a substantially similar X-ray diffractogram to that shown in FIG. 4, for example there are characteristic peaks at 6.6, 8.0, 11.2, 13.1 degrees 2 theta and a substantially similar solid state $^{13}$C-NMR spectrum to that shown in FIG. 7 for example with characteristic peaks at 154.3, 149.3, 141.6, 138.5 ppm.

Form B substantially free of solvent may be distinguished from other forms by the following analytical data, i.e., it has a melting point of about 138° C. when obtained in similar purity to the material described in Example 7 which may be determined by conventional methods such as HPLC and significant IR bands (FIG. 2) at about 538, 574, 614, 675, 722, 762, 782, 815, 833, 884, 925, 938, 970, 986, 1006, 1039, 1069, 1094, 1114, 1142, 1182, 1230, 1274, 1304, 1488, 1510, 1574, 1604, 1631 $cm^{-1}$.

The DSC exotherm, measured at 10° C. per minute, shows a maximum of about 137° C. in both open and closed pans. Form B also has a substantially similar X-ray diffractogram to that shown in FIG. 5, for example, there are characteristic peaks at 5.7, 11.3, 12.4, 14.3 degrees 2 theta and a substantially similar solid state $^{13}$C-NMR spectrum to that shown in FIG. 8, for example with characteristics peaks at 154.6, 148.3, 150.1, 141.7, 142.7, 139.0 ppm.

Figure 3A:
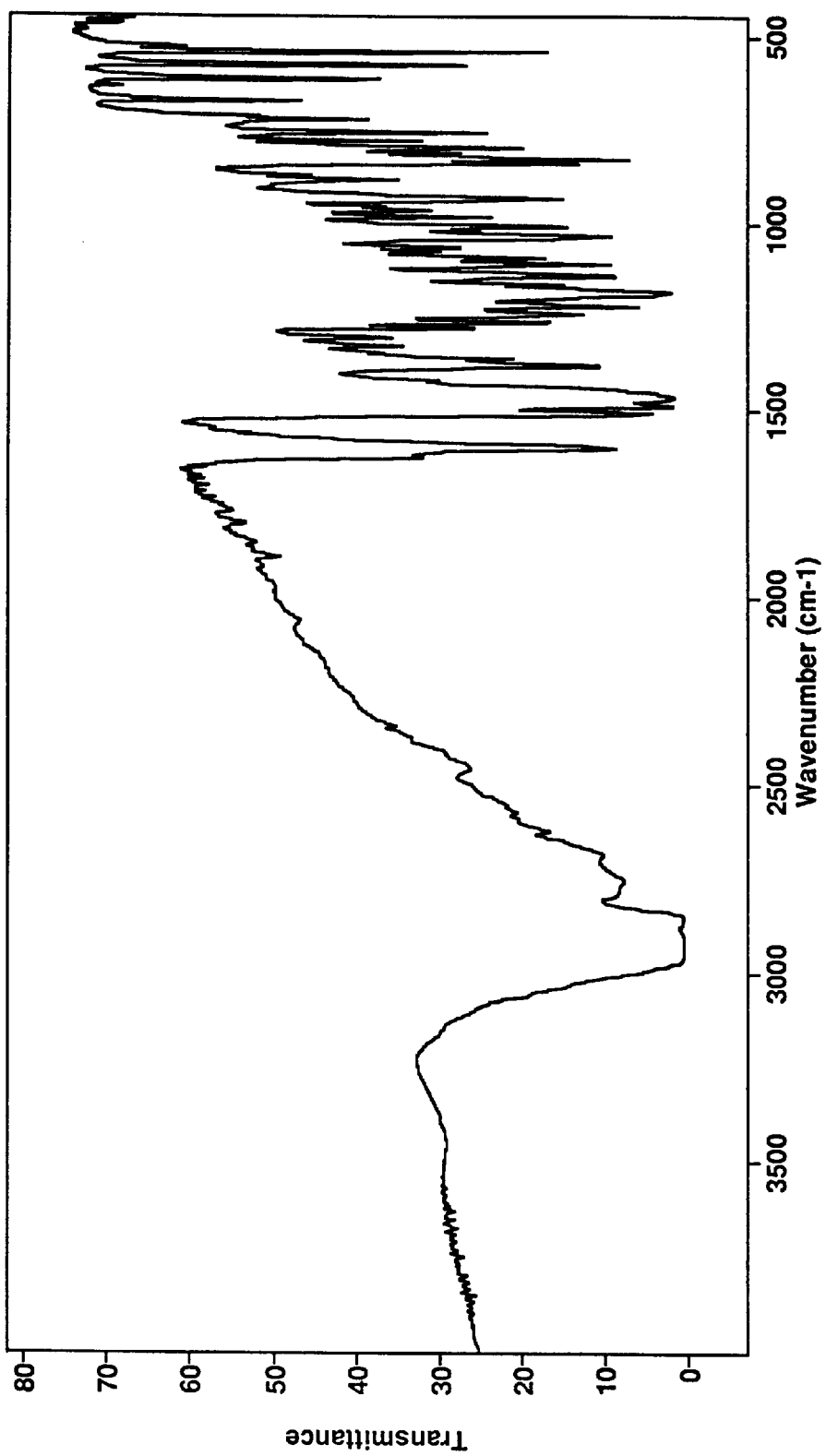
FIGS. 3A and 3B are IR absorbtion spectra for Form C.
Figure 3B:
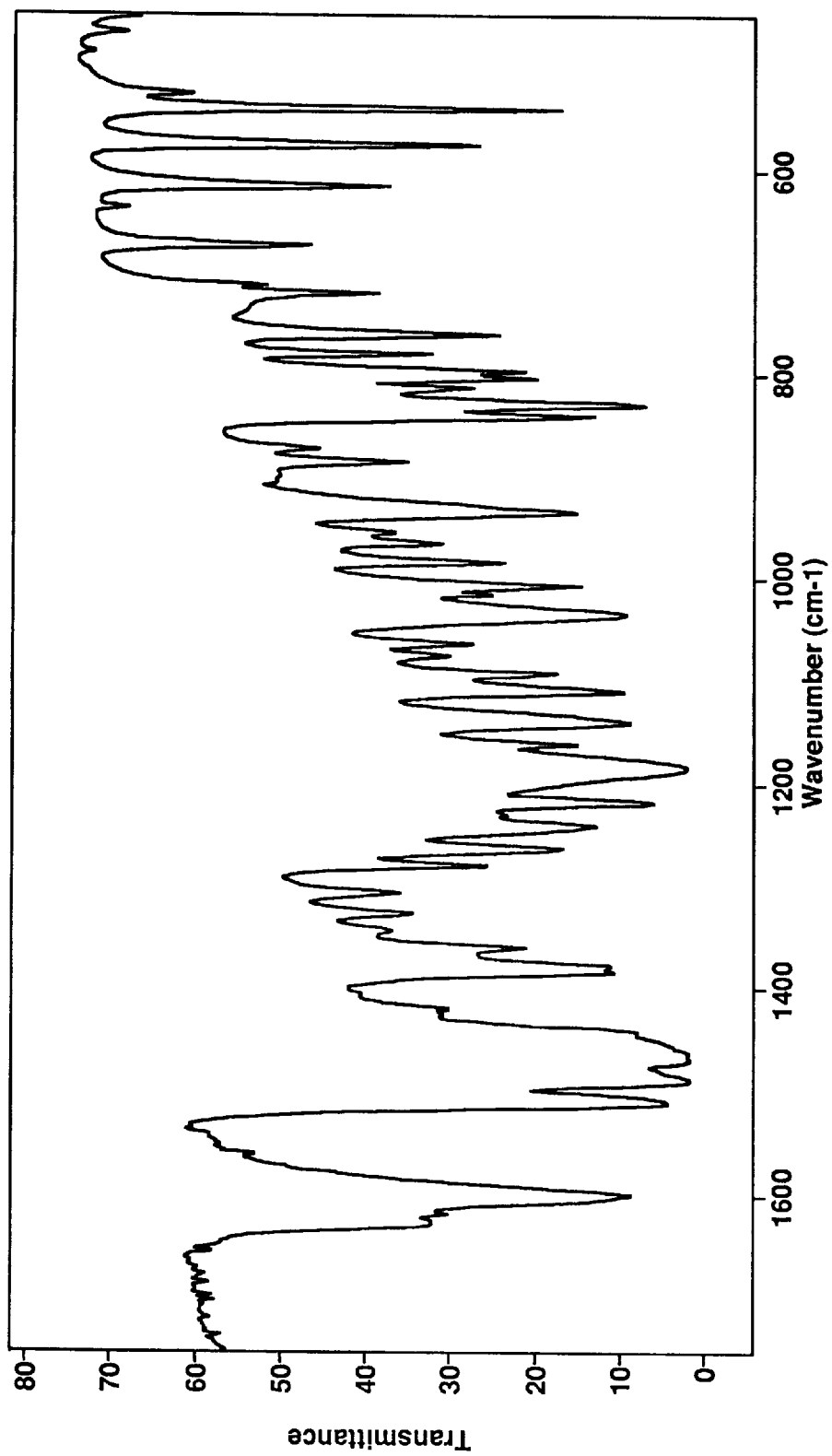

Form C may be distinguished from other forms by the following analytical data, i.e. it has a melting point of about 164° C. when obtain in similar purity to the material described in Example 8 which may be determined by conventional methods such as HPLC and has significant IR bands (FIG. 3) at about 540, 574, 615, 674, 720, 760, 779, 802, 829, 840, 886, 935, 965, 984, 1007, 1034, 1092, 1109, 1139, 1183, 1218, 1240, 1263, 1280, 1507, 1540, 1558, 1598, 1652 $cm^{-1}$.

The DSC exotherm, measured at 10° C. per minute, shows a maximum of about 161° C. in both open and closed pans.

Figure 6:
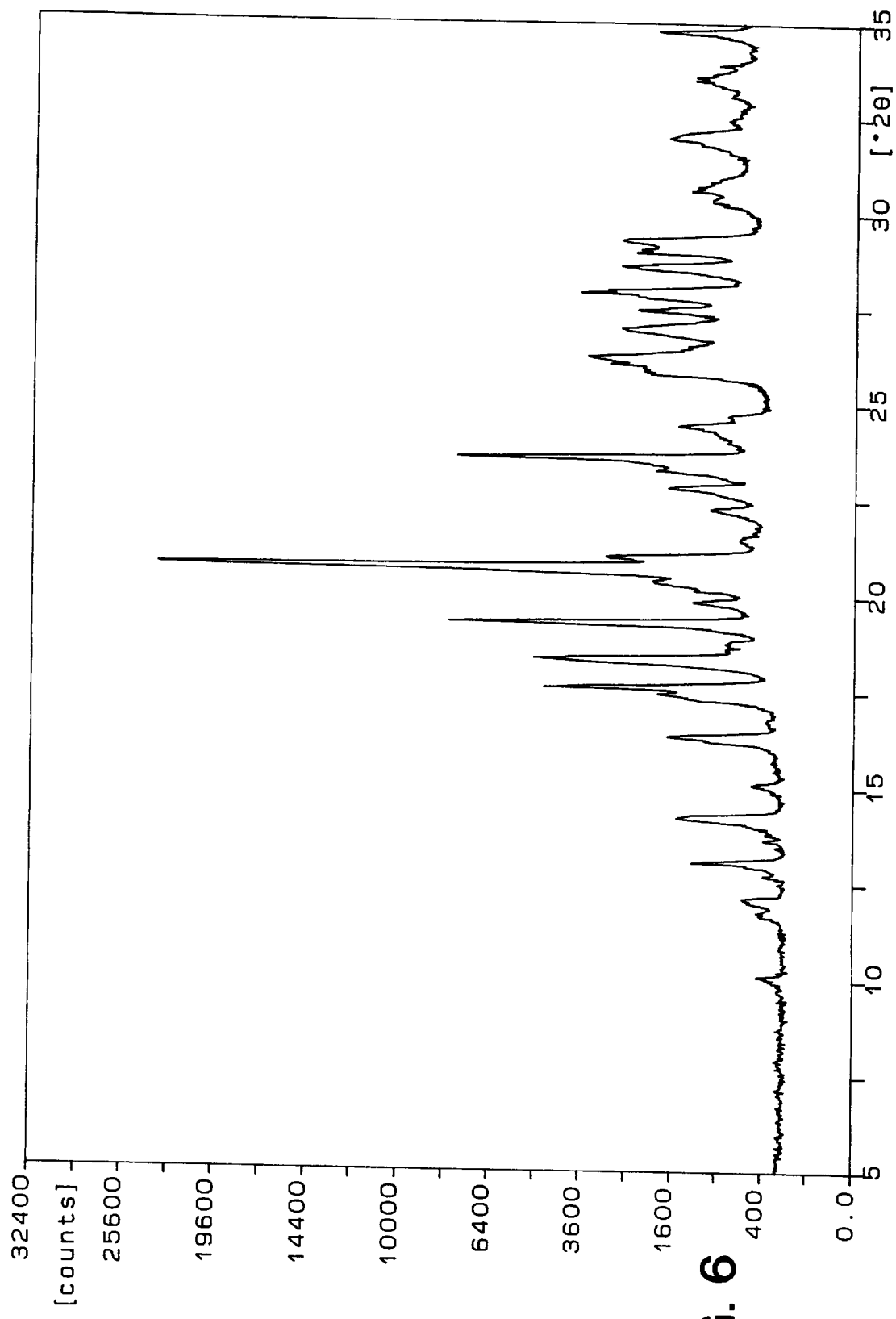
FIG. 6 is an x-ray diffractogram for Form C.

Form C also has a substantially similar X-ray diffractogram to that shown in FIG. 6, for example there are characteristic peaks at 10.1, 12.1, 13.1, 14.3 degrees 2 theta and a substantially similar solid state $^{13}$C-NMR spectrum to that in FIG. 9, for example with characteristic peaks at 154.0, 148.5, 143.4, 140.4 ppm.

Form D may be distinguished from other forms by the following analytical data in that it exists as a semi-crystalline solid with a melting point of about 125° C. when obtained in similar purity to the material described in Example 14 which may be determined by conventional methods such as HPLC.

Form D may also be characterized in that it has essentially similar physical characteristics when prepared from a toluene precursor solvate using methods generally described herein said toluene precursor solvate having significant IR bands at about 1631, 1603, 1555, 1513, 1503, 1489, 1340, 1275, 1240, 1221, 1185, 1168, 1140, 1113, 1101, 1076, 1037, 1007, 986, 968, 935, 924, 885, 841, 818, 783, 760, 742, 720, 698, 672, 612, 572, 537 and 465 $cm^{-1}$, and characteristic X-ray diffraction peaks at 7.2, 9.3, 12.7 and 14.3 degrees 2 theta.

The question of which particular form a particular sample of paroxetine hydrochloride anhydrate is would be readily determined by one skilled in the art using conventional techniques with reference to the data provided above that given in the examples and any other conventional means.

Preferably forms A and B exist as needles and form C exits as needles or prisms.

The present invention also provides a process for the preparation of paroxetine hydrochloride anhydrate substantially free of propan-2-ol which comprises crystallizing paroxetine hydrochloride in either;

i) an organic solvent or mixture of organic solvents which form a solvate with the paroxetine hydrochloride and which are not removable by conventional drying techniques; or ii) an organic solvent or mixture or organic solvents which do or do not form a solvate with the paroxetine hydrochloride but which are removable by conventional vacuum oven drying;

thereafter in the case of i) displacing the solvated solvent or solvents using a displacing agent and in the case of ii) by removing the solvent.

The present invention also provides a process for the preparation of the paroxetine hydrochloride solvates other than the propan-2-ol solvate which comprises crystallizing paroxetine hydrochloride in an organic solvent or mixture of solvents which form a solvate with the paroxetine hydrochloride and which are not removable by conventional drying techniques.

The present invention also provides a process for the preparation of paroxetine hydrochloride anhydrate substantially free of bound organic solvent which comprises crystallizing paroxetine hydrochloride in an organic solvent and displacing the solvated solvent or solvents from the paroxetine hydrochloride solvate using a displacing agent.

In one preferred aspect of the invention crystallization of paroxetine hydrochloride anhydrate is achieved by contacting a solution of paroxetine free base in an organic solvent or solvents with dry hydrogen chloride gas.

Alternatively, prior to the crystallization of the paroxetine hydrochloride water may be removed from a solution of the paroxetine hydrochloride by azeotropic distillation of the solution. Suitable solvents therefore include those which form an azeotrope with water such as pyridine, toluene, and propan-2-ol. It should also be appreciated that mixtures of solvents can also be used to aid the azeotropic removal of water.

Thus, in another aspect of the invention paroxetine hydrochloride anhydrate is crystallized by dissolving paroxetine hydrochloride hemi-hydrate in an appropriate solvent substantially free of water which forms an azeotrope with water. Suitably solvent is removed by distillation and fresh solvent substantially free of water is added until all of the water is removed.

Paroxetine hydrochloride hemi-hydrate or the free base thereof may be prepared according to the procedures generally outlined in U.S. Pat. No. 4,721,723.

The organic solvents should be substantially free of water to the extent that there is insufficient water present at the time of crystallization to effect conversion to the hydrochloride hemi-hydrate. Organic solvents which are substantially free of water may be obtained in conventional manner. For example they can be dried using conventional techniques such as drying over molecular sieves or they can be purchased.

Factors which affect which form of the product that will be obtained include the particular choice of organic solvent or solvents. It should also be appreciated that the method of solvent removal also affects the particular form of the product which is desired.

For process variant i) it should be appreciated that the organic solvent or solvents which form a solvate with the crystallized paroxetine hydrochloride and which are not removable by conventional drying techniques may be determined by a matter of routine experimentation. Examples of such organic solvents include, but in no way are limited to, alcohols especially alkanols such as propan-2-ol, ethanol and propan-1-ol; organic acids such as acetic acid; organic bases such as pyridine; nitriles such as acetonitrile; ketones such as acetone; ethers such as tetrahydrofuran and chlorinated hydrocarbons such as chloroform.

The paroxetine hydrochloride solvate produced by process variant i) is suitably isolated and dried by conventional methods such as drying in vacuo to remove some or all of the free or unbound solvent. It should be appreciated that it is preferable and unexpected that the degree of drying is controlled such that only free solvent is removed. The bound solvent is then displaced with a displacing agent such as water or supercritical carbon dioxide. It is possible to use other displacing agents which may be selected by means of routine experimentation.

Preferably gaseous or liquid water may be used as a displacing agent. It is important that the paroxetine hydrochloride solvate is contacted with enough water and for sufficient time to displace the solvent but insufficient to cause conversion to the hydrochloride hemi-hydrate.

The amount of water, the form of the water, e.g., liquid or gaseous and the length of time which the paroxetine hydrochloride solvate is contacted with the water differs from solvate to solvate. This depends largely upon the solubility of the solvate in question.

Particular ratios of paroxetine hydrochloride solvate to water are outlined in the examples hereinafter described (Examples 1, 4 to 6, 9 to 11, 13 and 15). It should be appreciated that the pyridine solvate is believed to be more soluble in water than for example the propan-2-ol solvate. Thus the use of the common ion effect when using diluted hydrochloric acid may help prevent dissolution of the solvate and subsequent conversion to the hydrochloride hemi-hydrate.

After contact with water to displace the bound solvent the product is suitably dried, for example, in vacuo at elevated temperature. Suitable drying may be over a desiccant such as phosphorus pentoxide or potassium hydroxide.

When supercritical carbon dioxide is used it should be appreciated that the flow rate, temperature and pressure of the carbon dioxide may be controlled to give optimum solvent removal from the paroxetine hydrochloride solvate. Generally high pressure carbon dioxide may be used for example at about 2,500 psi. Elevated temperatures may also be preferably used such as between 50° to 80° C. More preferable between 55° to 75° C.

Process variant i) is preferably used to prepare Form A.

Preferably the crystallization of the paroxetine hydrochloride anhydrate Form A precursor solvate may be facilitated by the addition of seeds of paroxetine hydrochloride anhydrate Form A precursor solvate.

Alternatively, seeds of paroxetine hydrochloride anhydrate Form A may be used to facilitate the crystallization of paroxetine hydrochloride anhydrate Form A precursor solvates.

For process variant ii) it should be appreciated that an organic solvent or mixture of organic solvents which does or does not form a solvate with the paroxetine hydrochloride but which is removable by conventional vacuum oven drying may be determined by a matter of routine experimentation.

An example of a solvent which forms a bound solvate with the paroxetine hydrochloride but which is removable by conventional vacuum oven drying is toluene.

Toluene is preferably used to prepare Form D.

The crystallization of paroxetine hydrochloride anhydrate Form D precursor solvates may be facilitated by the addition of seeds of paroxetine hydrochloride anhydrate Form D precursor solvates.

Seeds of paroxetine hydrochloride anhydrate Form D may be used to facilitate the crystallization of paroxetine hydrochloride anhydrate Form D precursor solvates.

Examples of solvents which do not form a bound solvate with paroxetine hydrochloride but which are removable by conventional vacuum oven drying are butan-1-ol and ethyl acetate.

Butan-1-ol is preferably used to prepare Form B and that butan-1-ol or ethyl acetate are preferably used to prepare Form C.

If Form B is required this may be prepared according to or analogously to the procedures outlined in Example 7.

Preferably the use of seeds of Form B may be used to facilitate the crystallization of Form B.

If Form C is required this may be prepared according to or analogously to the procedures outlined in Examples 8 and 12.

It should also be appreciated that the use of seeds of Form C may be used to facilitate the crystallization of Form C.

Seed crystals of Forms A, B, C and D may be prepared according to the procedures described herein.

Paroxetine hydrochloride anhydrate substantially free of propan-2-ol and Forms A, B, C, and D (all of which are hereinafter referred to as the "products of the invention") can be used to treat and prevent the following disorders:

Alcoholism
Anxiety
Depression
Obsessive Compulsive Disorder
Panic Disorder
Chronic Pain
Obesity
Senile Dementia
Migraine
Bulimia
Anorexia
Social Phobia
Pre-Menstrual Syndrome (PMS)
Adolescent Depression
Trichotillomania
Dysthymia
Substance Abuse These disorders are herein after referred to as "the Disorders".

The present invention further provides a method for treating and/or preventing any one or more of the Disorders by administering an effective and/or prophylactic amount of the products of the invention to a patient in need thereof. The products of the invention can be used like paroxetine hydrochloride hemi-hydrate, which is approved in the United States for treatment of depression, as described in the PAXIL paroxetine hydrochloride package inserts. See, e.g., "PAXIL brand of paroxetine hydrochloride tablets," Physician's Desk Reference, published by Medical Economic Data Production Company, Montvale, N.J. ("PDR"), which is incorporated herein by reference as though fully set forth.

(PAXIL is a registered trademark of SmithKline Beecham.) The present invention further provides a pharmaceutical composition for use in the treatment and/or prevention of the Disorders which comprises the products of the invention and a pharmaceutically acceptable carrier.

The present invention also provides the use of the products of the invention for treating and/or preventing the Disorders.

The present invention also provides the use of the products of the invention in the manufacture of a medicament for treating and/or preventing the Disorders.

Preferably, the Disorders which are treated are depression, OCD and panic disorder.

The pharmaceutical compositions of this invention are usually adapted for oral administration, but formulations for dissolution for parental administration are also within the scope of this invention.

The composition is usually presented as a unit dose pharmaceutical composition containing from 1 to 200 mg of active ingredient calculated on a free base basis, more usually from 5 to 100 mg, for example 10 to 50 mg, preferably 20 to 50 mg, such as 10, 12.5, 15, 20, 25, 30 or 40 mg. Most preferably unit doses contain 20 mg of active ingredient calculated on a free base basis. Such a composition is normally taken from 1 to 6 times daily, for example 2, 3 or 4 times daily so that the total daily amount of active agent administered is within the range 5 to 400 mg, preferably 20 to 50 mg, of active ingredient calculated on a free base basis. Most preferably the unit dose is taken once a day. See, PDR, cited above.

Preferred unit dosage forms include tablets or capsules.

The compositions of this invention may be formulated by conventional methods of admixture such as blending, filling and compressing.

Suitable carriers for use in this invention include a diluent, a binder, a disintegrant, a coloring agent, a flavoring agent and/or preservative. These agents may be utilized in conventional manner, for example in a manner similar to that already used for marketed anti-depressant agents.

Specific examples of pharmaceutical compositions include those described U.S. Pat. No. 4,721,723, U.S. Pat. No. 4,007,196, and PDR, cited above, in which the products of the present invention are used as the active ingredients.

The following examples illustrate the present invention but are not limiting.

EXAMPLE 1

Crystalline Paroxetine Hydrochloride Anhydrate Substantially Free of Bound Propan-2-ol (Form A)

i) Paroxetine hydrochloride propan-2-ol solvate

Paroxetine hydrochloride hemi-hydrate [150 g] was stirred with propan-2-ol [1000 ml] and toluene [300 ml] in a round bottom flask and heated to boiling. Solvent was removed by distillation, the total volume being maintained by adding fresh propan-2-ol, until the boiling point had reached approximately 82° C., indicating that all the water had been removed.

The mixture was allowed to cool to approximately 50° C., when it spontaneously crystallized. The contents of the flask rapidly set to a thick paste which was diluted with propan-2-ol [approx. 500 ml] and stirred vigorously. The resulting suspension was allowed to cool to approximately 30° C. and filtered under vacuum, taking care to avoid the absorption of atmospheric moisture. The solvent-wet cake was dried in high vacuum over phosphorus pentoxide.

Yield of solvated paroxetine hydrochloride 151 g, propan-2-ol content 13.0% (estimated by $^1$H-NMR).

The infra-red spectrum (Nujol mull) showed inter alia a characteristic band at 667 cm$^{-1}$.

ii) Paroxetine hydrochloride anhydrate (Form A)

Paroxetine hydrochloride propan-2-ol solvate [110 g, propan-2-ol content 13.0%] was stirred in a beaker with water [275 ml] for 20 minutes. The mixture was filtered under vacuum and the damp solid dried in vacuum over phosphorus pentoxide to constant weight.

Yield of paroxetine hydrochloride anhydrate Form A 91.0 g

Water content 0.13% (KF), propan-2-ol content 0.05% (estimated by $^1$-HNMR).

Melting point: 123°–125° C.

The DSC exotherm, measured at 10° C. per minute, showed a maximum at about 126° C. using an open pan and a maximum at about 121° C. using a closed pan.

Figure 1A:
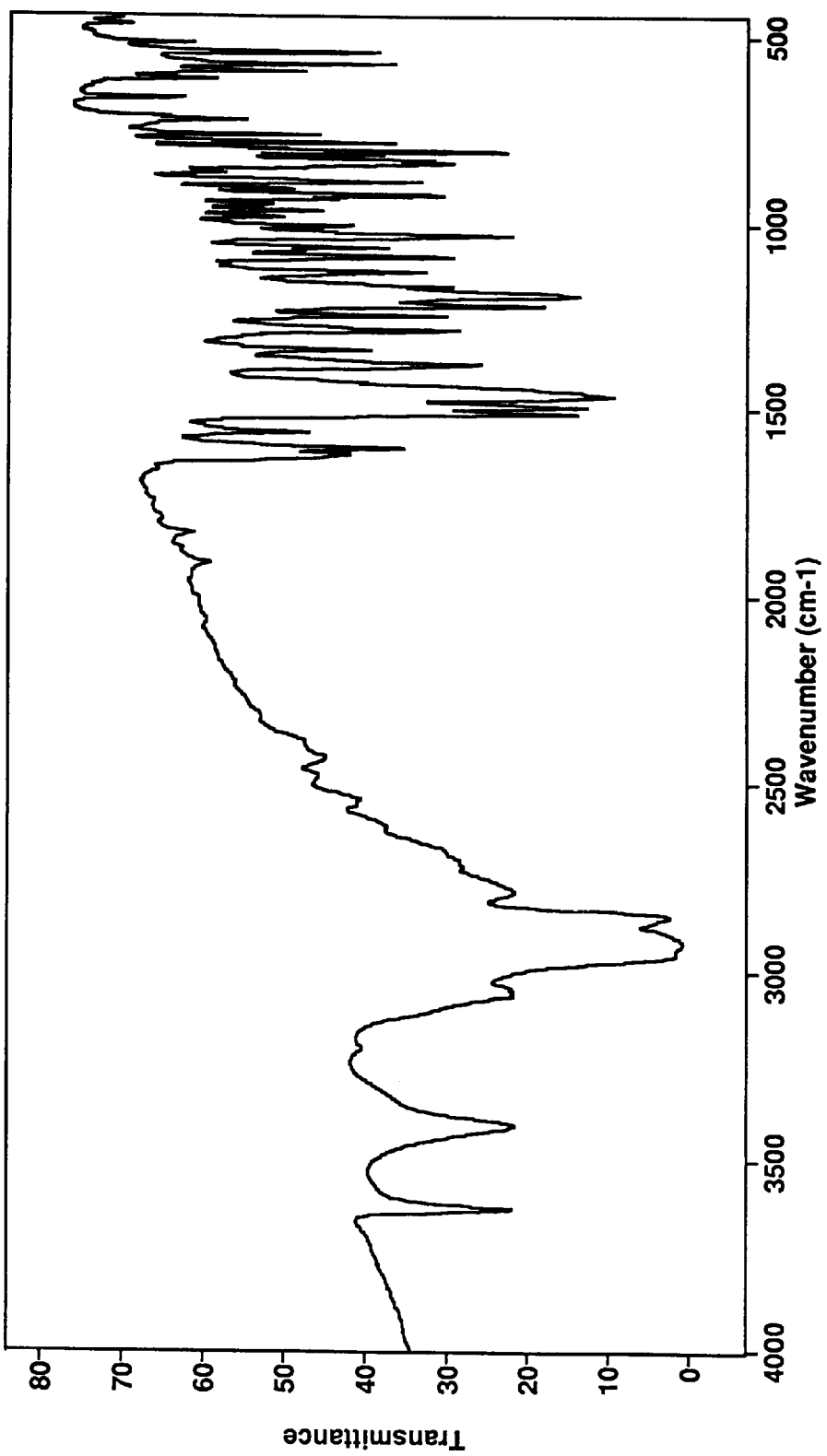
FIGS. 1A and 1B are IR absorbtion spectra for Form A.
Figure 1B:
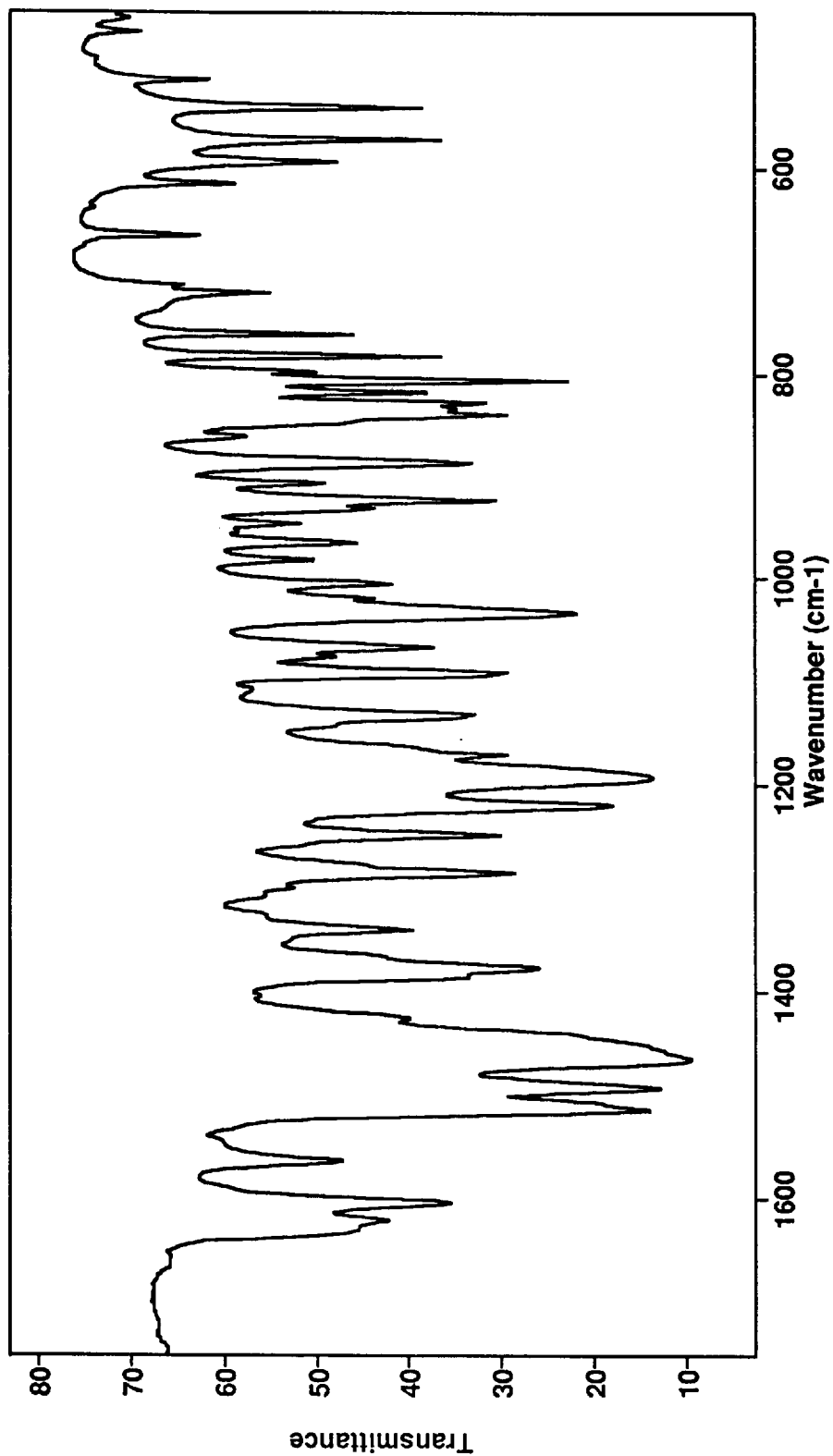

The infra-red spectrum [Nujol mull] showed inter alia characteristic bands at 665, 3631 and 3402 cm$^{-1}$ (see FIG. 1).

Elemental analysis:

Required for paroxetine hydrochloride anhydrate:

C 62.38 H 5.79 N 3.83%

Found: C 62.10 H 5.89 N 3.67%

Figure 7:
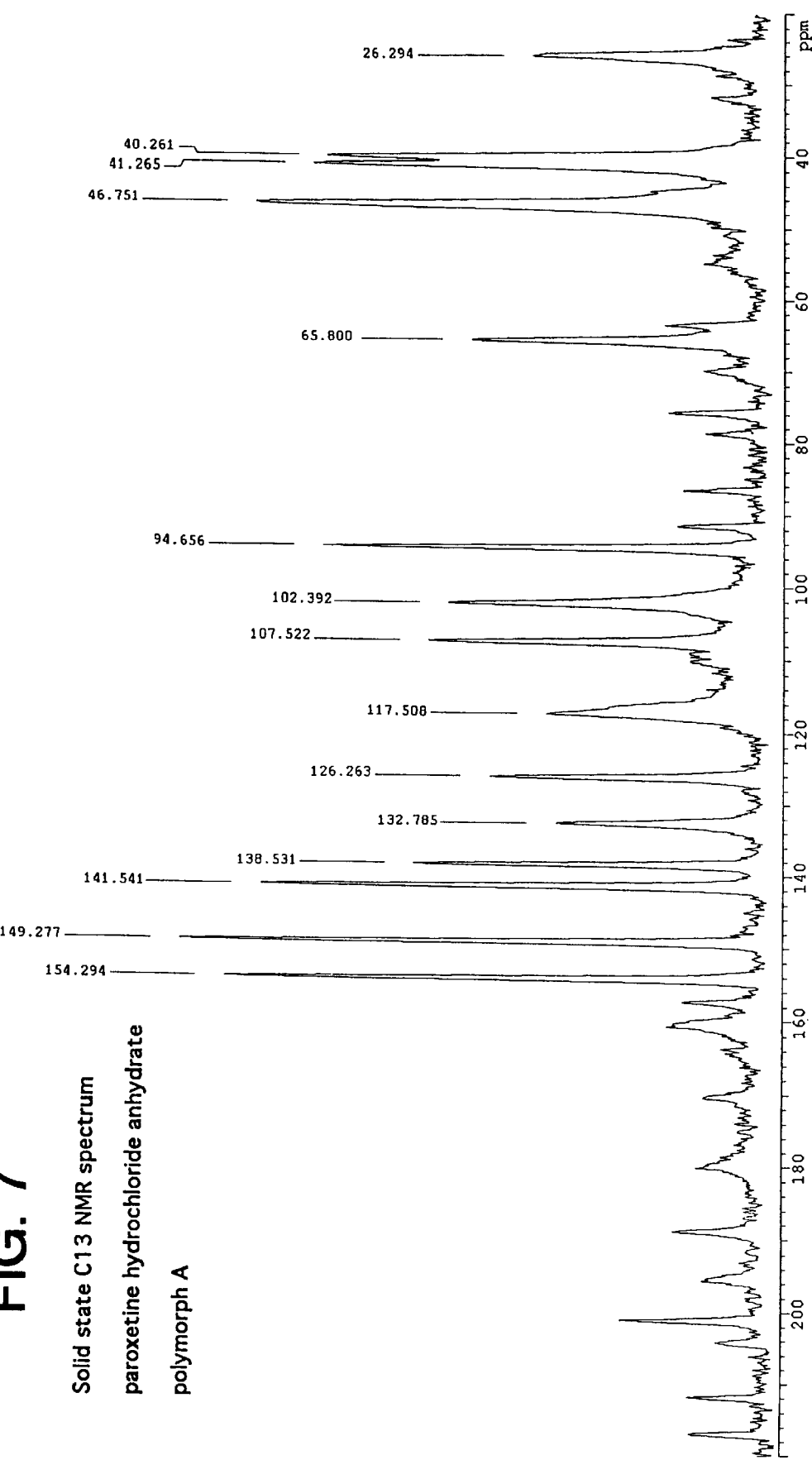
FIG. 7 is a solid state $^{13}$C-NMR spectra for Form A.

The sample was also examined by X-ray powder diffraction (see FIG. 4) and solid state $^{13}$C-NMR (see FIG. 7).

EXAMPLE 2

Paroxetine Hydrochloride Propan-2-ol Solvate

Paroxetine free base (42.09 g) was dissolved in propan-2-ol (Fisons SLR grade, 210 ml). Hydrogen chloride gas was bubbled into a cooled flask containing propan-2-ol (157 g) until 20.8 g hydrogen chloride had been absorbed. 39 g of this solution (containing approximately 4.6 g hydrogen chloride) was added rapidly to the paroxetine solution and the mixture stirred briskly. After about 1 minute crystallization began and the mixture rapidly set to an unstirrable paste, which was allowed to stand for one hour. The product was collected by filtration, washed with propan-2-ol (50 ml) and dried under vacuum at ambient temperature to constant weight in a desiccator containing phosphoric oxide. The sample was analyzed by $^1$H-NMR spectrometry and found to contain approximately 6% propan-2-ol by weight. Part of the sample was placed in a vacuum oven set at 50° C. and further dried to constant weight, which took a further 4 days. $^1$H-NMR spectrometry showed that the sample contained approximately 2% propan-2-ol by weight.

EXAMPLE 3

Paroxetine Hydrochloride Propan-2-ol Solvate

Paroxetine free base (52.37 g) was dissolved in dry propan-2-ol (250 ml) and a solution of hydrogen chloride gas in dry propan-2-ol (50 g of solution, containing approximately 5.8 g hydrogen chloride) was added rapidly with brisk stirring. After about 30 seconds crystallization commenced, and the mixture was stirred for a further 30 minutes at ambient temperature to permit complete crystallization. The product was isolated by vacuum filtration, washed with 25 ml dry propan-2-ol, and dried in a desiccator containing phosphoric oxide at ambient temperature under vacuum.

After 3 days a sample was analyzed by $^1$H-NMR and found to contain 10.5% propan-2-ol. The rest of the material was dried for a further 3 days to constant weight under vacuum with fresh phosphoric oxide in the desiccator.

$^1$H-NMR analysis showed that the product contained 5.7% w/w propan-2-ol.

EXAMPLE 4

Crystalline Paroxetine Hydrochloride Anhydrate Substantially Free of Bound Pyridine (Form A)

i) Preparation of paroxetine hydrochloride pyridine solvate

Paroxetine hydrochloride containing ca. 2% propan-2-ol [20.0 g] was dissolved in hot pyridine [200 ml] and some of the solvent removed by distillation. The flask was sealed and allowed to cool, whereupon the pale red solution spontaneously crystallized. The thick suspension was stirred well, filtered, avoiding excessive exposure to atmospheric moisture, and the solid washed on the filter with pyridine [25 ml]. The product was dried under high vacuum over phosphorus pentoxide.

Yield 22.0 g.

Microscopic examination showed the product to be in the form of needle crystals, and analysis by $^1$H-NMR showed the presence of 15.2% by weight of pyridine (theory for a 1:1 solvate 17.77%). The infra-red spectrum (Nujol mull) of the pyridine solvate differed from both that of hemi-hydrate and anhydrate Form A and in particular showed no significant bands in the 3000 cm$^{-1}$ region. The pyridine solvate also gave a distinctive X-ray powder diffraction pattern.

ii) Preparation of paroxetine hydrochloride anhydrate (Form A)

Paroxetine hydrochloride pyridine solvate [5.00 g] was added to 5 molar hydrochloric acid [25 ml] in a beaker and stirred for 5 minutes. The mixture was filtered, drained well, and washed with water [15 ml]. The crystals were dried under high vacuum over phosphorus pentoxide.

Yield 4.00 g

The infra-red spectrum (Nujol mull) was consistent with paroxetine hydrochloride anhydrate Form A, and no pyridine could be detected by $^1$H-NMR analysis.

EXAMPLE 5

Paroxetine Hydrochloride Anhydrate Substantially Free of Bound Acetic Acid (Form A)

i) Preparation of paroxetine hydrochloride acetic acid solvate

Paroxetine hydrochloride containing approximately 2% propan-2-ol [30.0 g] was dissolved in hot glacial acetic acid [120 ml] and some of the solvent removed by distillation. The flask was sealed and allowed to cool overnight. The clear pale yellow solution was seeded with paroxetine hydrochloride anhydrate Form A, ultrasonicated and stirred at room temperature for several hours. The mixture was allowed to stand for 24 hours, filtered and the product dried under high vacuum in a desiccator containing potassium hydroxide.

Yield 17.29 g.

Analysis by $^1$H-NMR showed the presence of 13.5% by weight of acetic acid (theory for a 1:1 solvate 14.10%). The infra-red spectrum (Nujol mull) of the acetic acid solvate differed from both that of paroxetine hydrochloride hemihydrate and anhydrate Form A and in particular showed a strong band at 1705 cm$^{-1}$ indicative of bound acetic acid and no significant bands in the 3000 cm$^{-1}$ region. The acetic acid solvate also gave a distinctive X-ray powder diffraction pattern.

ii) Preparation of paroxetine hydrochloride anhydrate (Form A)

Paroxetine hydrochloride acetic acid solvate [1.00 g] was treated with 5 molar hydrochloric acid [5 ml] and stirred for 5 minutes. The mixture was filtered, drained well, and the crystals dried under high vacuum in a desiccator containing phosphorus pentoxide.

Yield 0.80 g

The infra-red spectrum (Nujol mull) confirmed that the product was paroxetine hydrochloride anhydrate Form A. Analysis by $^1$H-NMR showed the presence of approximately 0.4% acetic acid. Microscopic examination showed the material to be in the form of fragmented needles.

EXAMPLE 6

Paroxetine Hydrochloride Anhydrate Substantially Free of Bound Acetonitrile (Form A)

i) Preparation of paroxetine hydrochloride acetonitrile solvate

Paroxetine hydrochloride anhydrate Form A prepared using the method of Example 1 (10.8 g) was dissolved in warm anhydrous acetonitrile (40 ml) in a conical flask, sealed, and cooled in the refrigerator for 1 hour, during which time some crystals separated. The mixture was ultrasonicated, returned to the refrigerator, and left overnight. The contents set to a thick paste. The following morning the paste was broken up using vigorous shaking and ultrasonication, and the mixture filtered. The product was dried under high vacuum in a desiccator containing phosphorus pentoxide.

Yield 9.30 g, acetonitrile content 2.5% (by $^1$H-NMR).

ii) Preparation of paroxetine hydrochloride anhydrate (Form A)

Paroxetine hydrochloride acetonitrile solvate (4.23 g) was stirred in water (20.6 g) for 10 minutes. The solid was collected by vacuum filtration, washed on the filter with water (10 ml) and dried in a vacuum oven containing phosphorus pentoxide at 50° C.

Yield 3.75 g

The IR spectrum showed that the product was paroxetine hydrochloride anhydrate Form A.

Acetonitrile content approximately 0.5% (by $^1$H-NMR).

EXAMPLE 7

Paroxetine Hydrochloride Anhydrate (Form B)

Paroxetine free base [10.0 g] was dissolved in butan-1-ol [25 ml] at room temperature and a solution of hydrogen chloride gas [1.25 g] in butan-1-ol [15 ml] was added. The clear pale red/brown solution was sealed and stored in the refrigerator overnight. A small amount of crystalline material formed on the base of the flask and ultrasonication was used to bring about crystallization of the bulk. The mixture was again stored in the refrigerator overnight, then allowed to warm to room temperature and filtered. The product was dried under high vacuum in a desiccator containing phosphorus pentoxide.

Microscopic examination with a polarizing microscope showed the sample to be in the form of feather shaped crystals.

Melting point: 137°–138° C.

The $^1$H-NMR (CDCl$_3$) spectrum conformed to that of a standard sample of paroxetine hydrochloride.

The elemental analysis was consistent with anhydrous paroxetine hydrochloride:

Required for $C_{19}H_{21}NClFO_3$: C 62.38 H 5.79 N 3.83 Cl 9.69%

Found: C 62.08 H 5.75 N 3.81 Cl 9.62%

Figure 5:
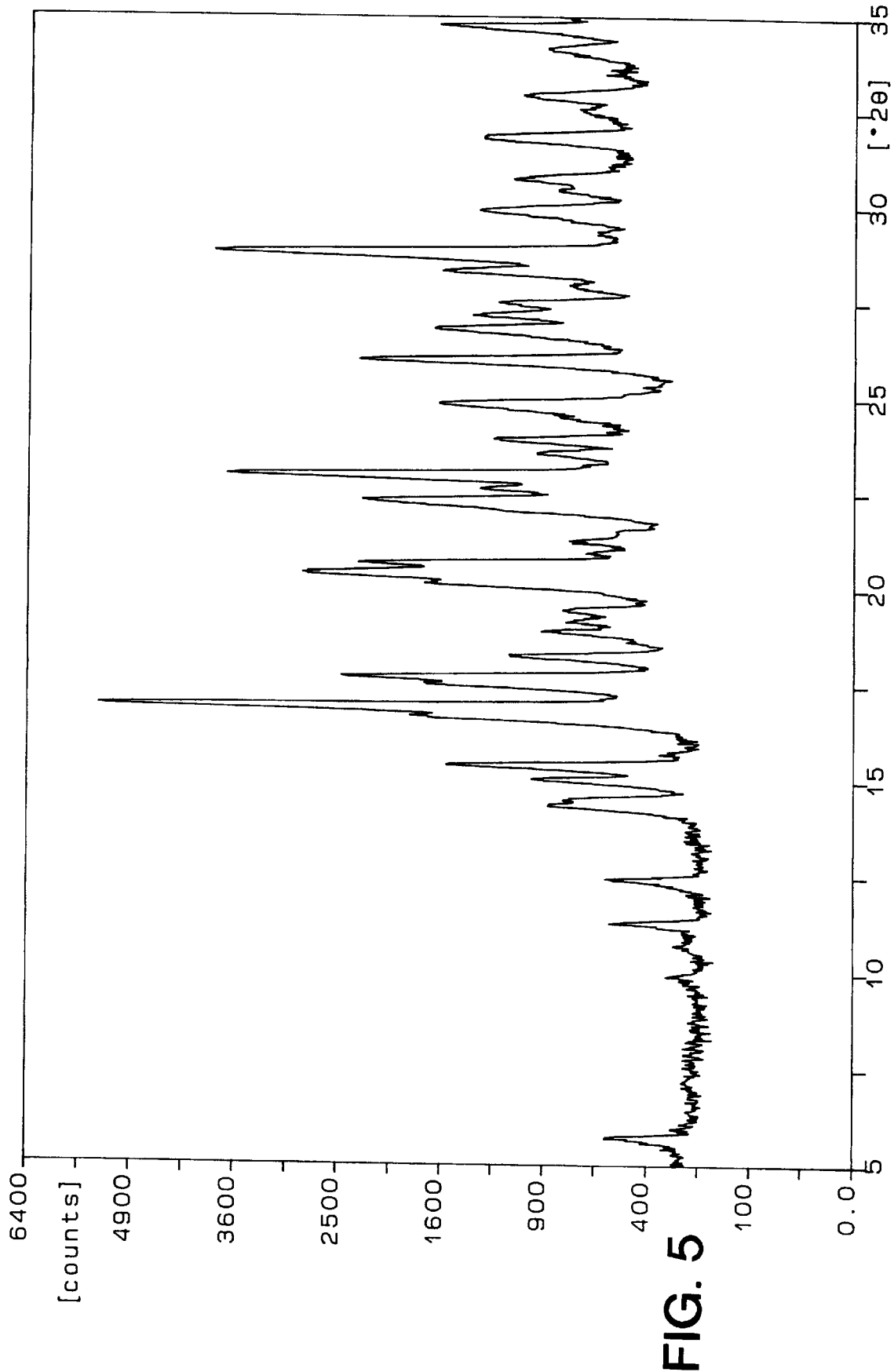
FIG. 5 is an x-ray diffractogram for Form B.

The X-ray powder diffractogram confirmed that the sample was crystalline (see FIG. 5). The diffractogram differed from both that of hemi-hydrate and anhydrate Form A.

Figure 2A:
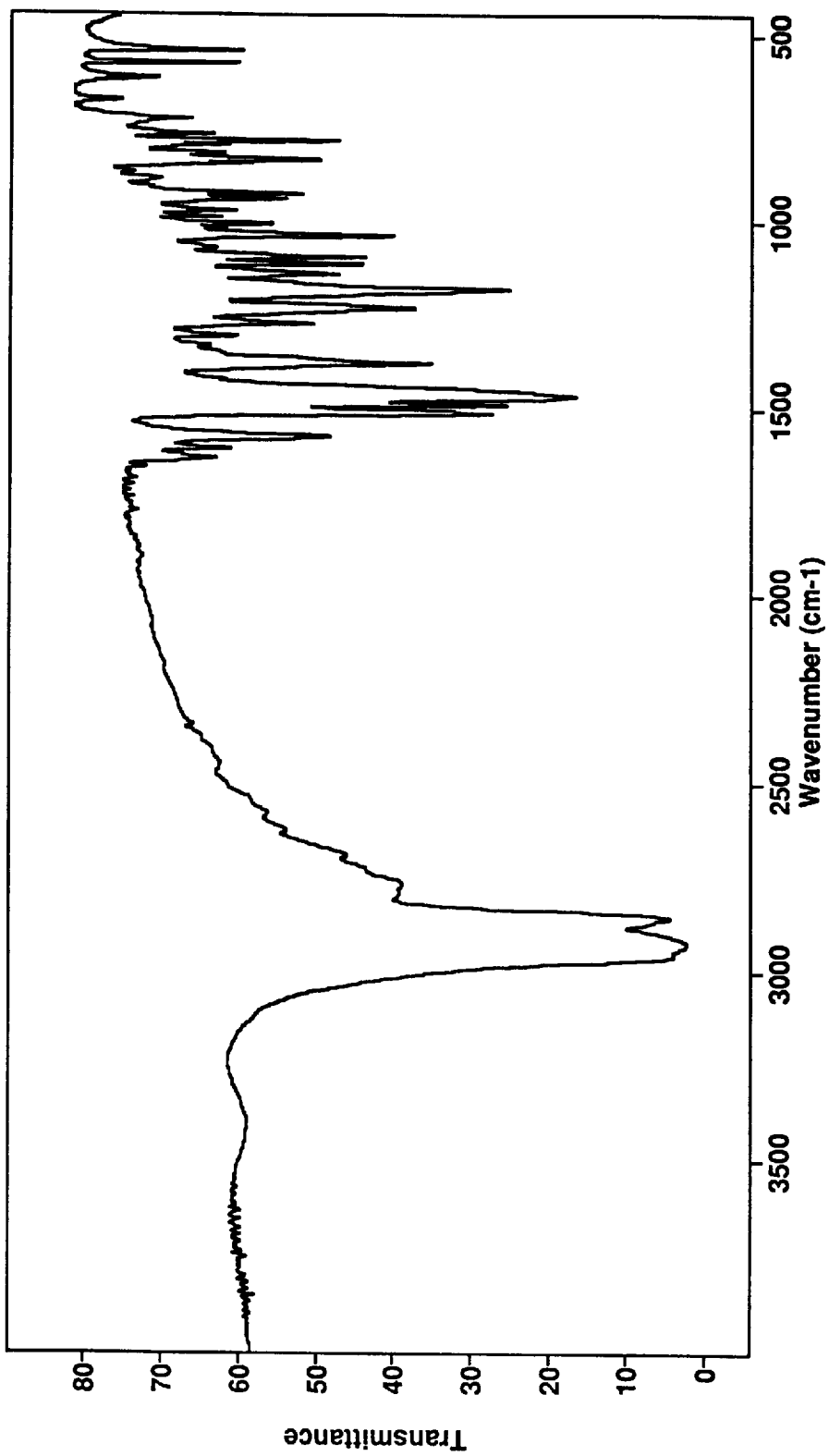
FIGS. 2A and 2B are IR absorbtion spectra for Form B.
Figure 2B:
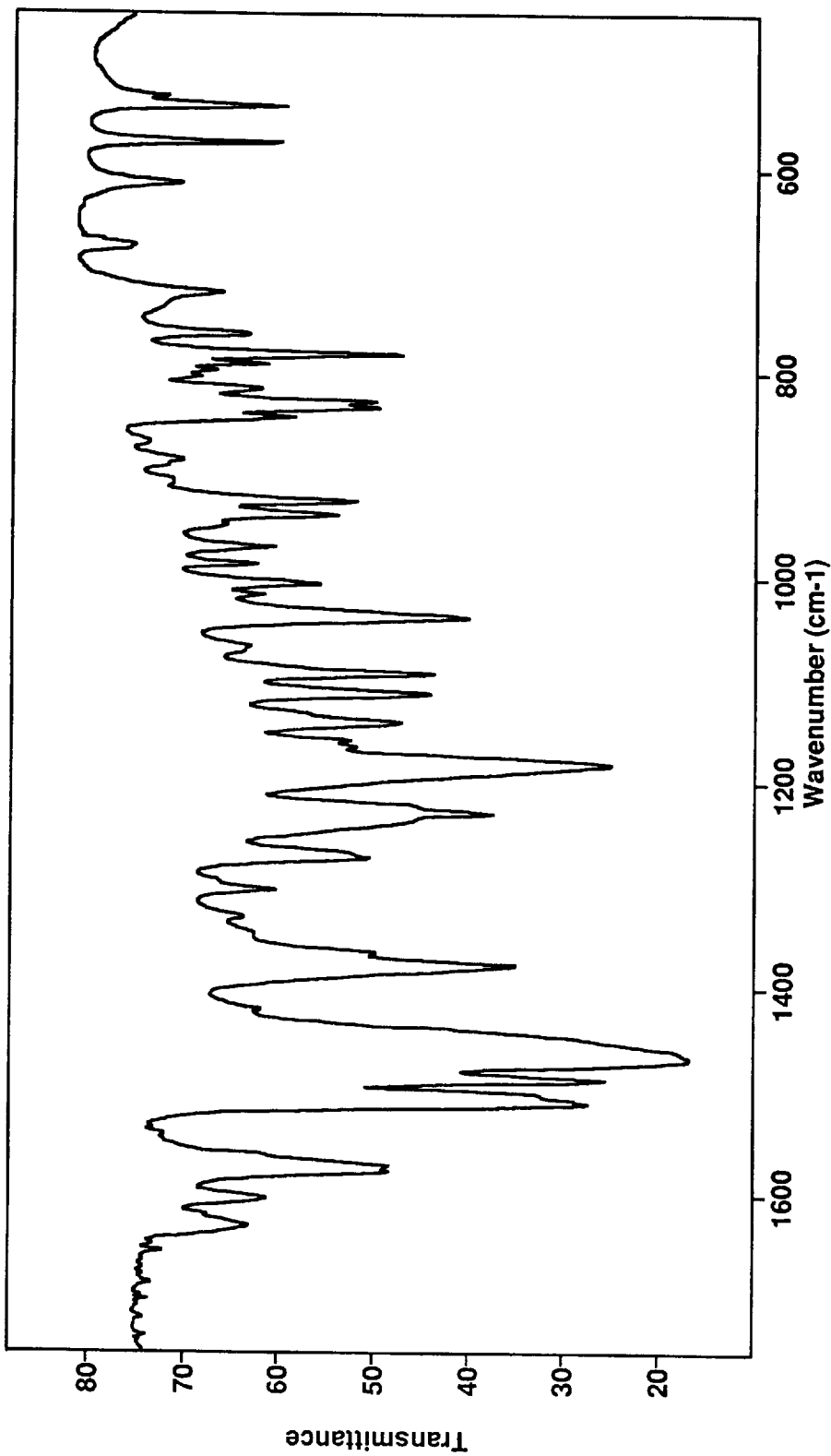

The IR spectrum (Nujol mull) also differed from both that of hemi-hydrate and anhydrate Form A (see FIG. 2).

The DSC exotherm, measured at 10° C. per minute, showed a maximum at about 137° C. in both open and closed pans.

Figure 8:
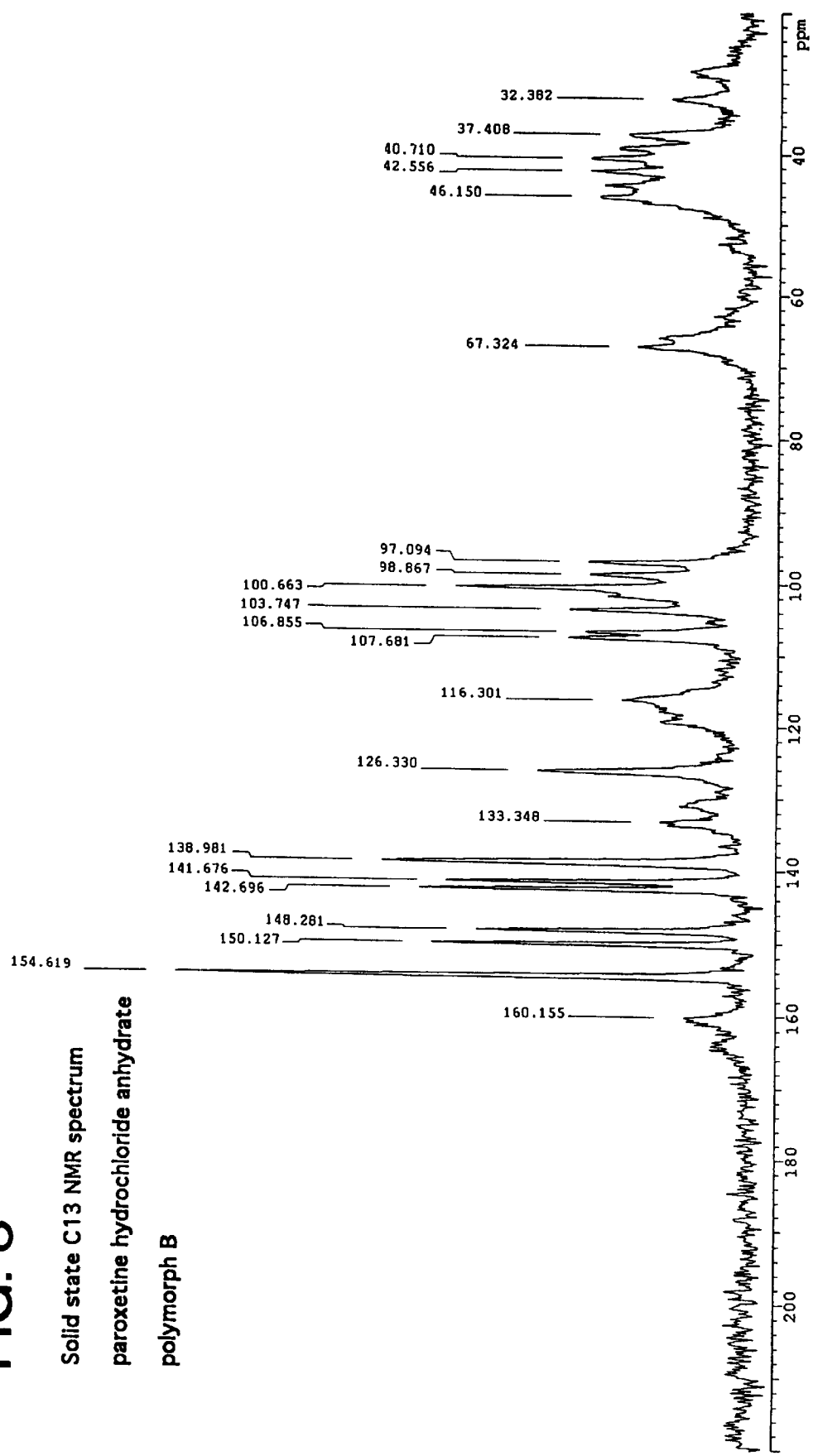
FIG. 8 is a solid state $^{13}$C-NMR spectra for Form B.

The sample was also examined by solid state $^{13}$C-NMR (see FIG. 8).

EXAMPLE 8

Paroxetine Hydrochloride Anhydrate (Form C)

Paroxetine hydrochloride hemi-hydrate [300 g] and toluene. [1200 ml] were heated under reflux and the water removed using a Dean and Stark apparatus. When no further water could be collected, the bulk of the toluene was removed by distillation and replaced with anhydrous butan-1-ol. Distillation was continued until the still temperature reached about 117° C., indicating that all the toluene had been removed. The mixture was diluted to about 1200 ml with butan-1-ol and allowed to cool. At about 42° C., seeds of paroxetine hydrochloride anhydrate Form B (needles) were added. Although crystallization then began, it was observed that the product was in the form of well formed prisms, indicating that the product was crystallizing in a different form to the seeds added.

The mixture was allowed to stand overnight, then filtered. The crystals were washed on the filter with butan-1-ol, then dried in vacuum at 50° C. over phosphorus pentoxide.

Yield 250 g

Melting point: 162°–164° C.

Analysis by $^1$H-NMR (CDCl$_3$) confirmed that the product was paroxetine hydrochloride and showed the presence of a trace of butan-1-ol (ca 0.1% by weight ). The infra red spectrum (Nujol mull) differed from either Form A or B, (see FIG. 3).

Water content 0.06% (KF)

The elemental analysis was consistent with anhydrous paroxetine hydrochloride:

Required for $C_{19}H_{21}NC1FO$: C 62.38 H 5.79 N 3.83 Cl 9.69%

Found: C 62.23 H 5.67 N 3.83 Cl 9.74%

The DSC exotherm, measured at 10° C. per minute, showed a maximum at about 161° C. in both open and closed pans.

The X-ray powder diffractogram confirmed that the sample was crystalline (see FIG. 6). The diffractogram differed from both that of anhydrate Form A and anhydrate Form B.

The sample was also examined by solid state $^{13}$C-NMR (see FIG. 9).

EXAMPLE 9

Paroxetine Hydrochloride Anhydrate Substantially Free of Bound Acetone (Form A)

i) Paroxetine Hydrochloride Acetone solvate

Paroxetine free base (10.51 g) was dissolved in acetone (40 ml, dried with 4A molecular sieves), and a solution of hydrogen chloride gas (1.31 g) in dry acetone (10 ml) added with stirring. Crystallization occurred spontaneously within one minute, and the mixture quickly became unstirrable. After approximately half an hour the product was filtered, placed in a desiccator over phosphorus pentoxide, and dried at ambient temperature overnight.

Weight of product: 11.24 g. Acetone content (estimated by 1H-NMR) 4% wt/wt. The infra-red spectrum showed a characteristic band at 667 cm$^{-1}$.

Approximately half the product was placed in a vacuum oven set at 50° C. and dried further to constant weight. 1H-NMR analysis of the resulting product indicated the presence of 1.2% acetone wt/wt.

ii) Paroxetine Hydrochloride Anhydrate (Form A)

A sample of the acetone solvate (5.18 g) was stirred for 10 minutes in water (20 ml), filtered, and dried at 50° C. in a vacuum oven containing phosphorus pentoxide.

Weight of product: 4.63 g. 1H-NMR analysis indicated the presence of 0.6% acetone wt/wt. The infra-red spectrum corresponded to the spectrum of paroxetine hydrochloride anhydrate Form A and showed a characteristic band at 665 cm$^{-1}$.

EXAMPLE 10

Paroxetine Hydrochloride Anhydrate Substantially Free of Bound Ethanol (Form A)

i) Paroxetine Hydrochloride Ethanol Solvate

Paroxetine free base (11.25 g) was dissolved in absolute ethanol (40 ml), and a solution of hydrogen chloride gas (1.9 g) dissolved in absolute ethanol (20 ml) added with stirring. There was no sign of crystallization after 10 minutes, so the clear solution was seeded with paroxetine hydrochloride anhydrate Form A. After 30 minutes there was still no sign of crystallization, so the solution was evaporated at reduced pressure to approximately half volume and re-seeded. This time slow crystallization was observed, and the mixture was left for a further hour. The resulting crystalline mass was dried at ambient temperature in a vacuum desiccator containing phosphorus pentoxide.

Weight of product: 11.87 g. Ethanol content (estimated by 1H-NMR) 4% wt/wt. The infra-red spectrum showed a characteristic band at 667 cm$^{-1}$.

A small sample was placed in a vacuum oven set at 50° C. and dried further. 1H-NMR analysis of the resulting product indicated the presence of 0.7% ethanol wt/wt. The infra-red spectrum corresponded to the spectrum of paroxetine hydrochloride anhydrate Form A and showed a characteristic band at 665 cm$^{-1}$.

ii) Paroxetine Hydrochloride Anhydrate (Form A)

A sample of the ethanol solvate (5.3 g) was stirred for 10 minutes in water (20 ml), filtered, and dried overnight at ambient temperature in a desiccator containing phosphorus pentoxide.

Weight of product: 4.56 g. 1H-NMR analysis indicated the presence of less than 0.4% ethanol wt/wt. The infra-red spectrum corresponded to the spectrum of paroxetine hydrochloride anhydrate Form A and showed a characteristic band at 665 cm$^{-1}$.

EXAMPLE 11

Paroxetine Hydrochloride Anhydrate Substantially Free of Bound Chloroform (Form A)

i) Paroxetine hydrochloride chloroform solvate

Paroxetine free base (8.54 g) was dissolved in chloroform (30 ml), and a solution of hydrogen chloride gas (1.05 g) dissolved in chloroform (10 ml) added with stirring. There was no sign of crystallization after 5 minutes, so the clear solution was seeded with paroxetine hydrochloride anhydrate Form A. After 15 minutes there was still no sign of crystallization, so hydrogen chloride gas was bubbled through the solution until the orange color disappeared. After one hour signs of very slow crystallization could be seen, with large needle crystals visible to the eye. The mixture was left to crystallize in a stoppered flask for a further hour, then filtered and dried at ambient temperature in a vacuum desiccator containing phosphorus pentoxide.

Weight of product: 5.65 g. Chloroform content (estimated by 1H-NMR) 12.5% wt/wt. The infra-red spectrum showed a characteristic band at 667 cm$^{-1}$.

A small sample was placed in a vacuum oven set at 50° C. and dried further. 1H-NMR analysis of the resulting product indicated the presence of 3.4% chloroform wt/wt.

ii) Paroxetine hydrochloride anhydrate (Form A)

A sample of the chloroform solvate containing 12.5% chloroform (2.0 g) was stirred for 10 minutes in water (8 ml), filtered, and dried overnight in a vacuum oven at 50° C.

Weight of product: 1.09 g. 1H-NMR analysis indicated the presence of approximately 0.8% chloroform wt/wt. The infra-red spectrum corresponded to the spectrum of paroxetine hydrochloride anhydrate Form A and showed a characteristic band at 665 cm$^{-1}$.

EXAMPLE 12

Paroxetine Hydrochloride Anhydrate (Form C)

Paroxetine free base (8.5 g) was dissolved in ethyl acetate (40 ml) and hydrogen chloride gas was bubbled in until the weight of the flask and contents had increased by 1.1 g. There was no sign of crystallization after 15 minutes, so the clear solution was seeded with paroxetine hydrochloride anhydrate Form A. After stirring for a further one hour, signs of very slow crystallization could be seen. The mixture was left stirring overnight to crystallize in a stoppered flask, then filtered and dried at ambient temperature in a vacuum desiccator containing phosphorus pentoxide.

Weight of product: 7.56 g. Ethyl acetate content (estimated by 1H-NMR) 0.4% wt/wt. The infra-red spectrum was different from both paroxetine hydrochloride hemi-hydrate and anhydrate Form A and consistent with the infra-red spectrum obtained in Example 8.

EXAMPLE 13

Paroxetine Hydrochloride Anhydrate Substantially Free of Bound Propan-1-ol (Form A)

i) Preparation of paroxetine hydrochloride propan-1-ol solvate

Paroxetine free base [10.6 g] was dissolved in propan-1-ol [30 ml] and hydrogen chloride gas (1.25 g) passed into the solution. The warm solution was seeded with paroxetine hydrochloride anhydrate Form B and ultrasonicated, whereupon the pale red solution rapidly crystallized. The thick suspension was diluted with propan-1-ol (25 ml), filtered avoiding excessive exposure to atmospheric moisture, and the product dried in vacuum over phosphorus pentoxide.

Yield 10.3 g.

Analysis by 1H-NMR showed the presence of approximately 7% by weight of propan-1-ol. The infra-red spectrum (Nujol mull) showed that the product was not Form B, but a solvated species with a significant band at about 667 cm$^{-1}$. The propan-1-ol solvate also gave a distinctive X-ray powder diffraction pattern.

ii) Preparation of paroxetine hydrochloride anhydrate (Form A)

Paroxetine hydrochloride propan-1-ol solvate [5.24 g] was stirred in water [25 ml] for 10 minutes. The mixture was filtered and the product washed with water [10 ml]. The crystals were dried in high vacuum over phosphorus pentoxide at 50° C.

Yield 4.35 g

The infra-red spectrum (Nujol mull) confirmed that the product was the anhydrate Form A. Analysis by 1H-NMR showed the presence of ca 0.25% by weight of propan-1-ol.

EXAMPLE 14

Paroxetine Hydrochloride Anhydrate (Form D)

i) Preparation of paroxetine hydrochloride toluene solvate

Paroxetine hydrochloride hemi-hydrate [100 g] was stirred under reflux in toluene [1000 ml] and the water removed using a Dean and Stark apparatus. The solution was allowed to cool, seeded with paroxetine hydrochloride Form A, and ultrasonicated. Crystallization was not induced, but after stirring for 40 minutes at room temperature the contents of the flask suddenly set to a thick paste. The product was collected by filtration and dried in vacuum over phosphorus pentoxide.

Analysis of the product by 1H-NMR showed the presence of about 10% wt/wt of toluene. The toluene solvate gave a distinctive IR spectrum, showing a characteristic band at 672 cm$^{-1}$.

The above procedure was repeated, seeding with the toluene solvate, and the product dried in vacuum over phosphorus pentoxide.

Yield of toluene solvate 106.7 g

Analysis of the product by 1H-NMR showed the presence of about 10% wt/wt of toluene. The product gave a distinctive X-ray powder diffractogram.

ii) Desolvation of the toluene solvate

The toluene solvate [20.0 g] was heated for 18 hours at 80° C. in vacuum over phosphorus pentoxide. Analysis by 1H-NMR showed the presence of about 0.3% wt/wt of toluene.

Water content: 0.08% (KF)

Melting point:. ca 125° C.

EXAMPLE 15

Paroxetine Hydrochloride Anhydrate Substantially Free of Bound Tetrahydrofuran (Form A)

i) Paroxetine hydrochloride tetrahydrofuran solvate.

Paroxetine free base (10.26 g) was dissolved in dry tetrahydrofuran (35 ml), and a solution of hydrogen chloride gas (1.3 g) dissolved in dry tetrahydrofuran (15 ml) added with brisk stirring. After a short period when the solution remained clear, rapid crystallization commenced so that within a few minutes the mixture became unstirrable. After a further half hour, the product was collected by filtration and dried at ambient temperature in a vacuum desiccator containing phosphorus pentoxide. Weight of product: 12.31 g. Tetrahydrofuran content (estimated by 1H-NMR) 11.4% wt/wt. The infra-red spectrum showed a characteristic solvate band at 667 cm$^{-1}$.

A small sample was placed in a vacuum oven set at 50° C. and dried over the weekend. 1H-NMR analysis of the resulting product indicated the presence of 1.3% tetrahydrofuran wt/wt.

ii) Paroxetine hydrochloride anhydrate (Form A)

A sample of the tetrahydrofuran solvate containing 11.4% tetrahydrofuran (5.0 g) was stirred for 10 minutes in water (20 ml), filtered, and dried in a vacuum oven at 50° C.

Weight of product: 3.79 g. 1H-NMR analysis indicated the presence of approximately 0.02% tetrahydrofuran wt/wt. The infra-red spectrum corresponded to the spectrum of paroxetine hydrochloride anhydrate Form A and showed a characteristic band at 665 cm$^{-1}$.

EXAMPLE 16

Paroxetine Hydrochloride Anhydrate Substantially Free of Bound Propan-2-ol (Form A)

Paroxetine hydrochloride propan-2-ol solvate (70 mg, containing 11.6% propan-2-ol) (Examples 2 or 3) was treated with a stream of carbon dioxide (3 ml/minute, 55° C. and 2,500 psi). After 30 minutes the propan-2-ol content was reduced to 5.2%, and after a total of 120 minutes it was further reduced to 0.4%. The temperature was then raised to 75° C., and after 30 minutes the propan-2-ol content was found to be 0.13%. After a further 60 minutes at 75° C. the propan-2-ol content was 0.07%.

In a separate experiment 70 mg of propan-2-ol solvate was extracted with carbon dioxide (3 ml/minute, 75° C. and 2,500 psi). After 150 minutes the propan-2-ol content was found to be 0.19%.

This experiment was repeated on a larger sample of the solvate (350 mg) under the same conditions, and the propan-2-ol content was found to be 0.16% after 150 minutes.

EXAMPLE 17

Crystallization of paroxetine hydrochloride anhydrate Form C from 2-butanone by seeding Paroxetine hydrochloride anhydrate Form C [7.0 g] was heated to boiling in anhydrous 2-butanone [40 ml] and the solution allowed to cool to ca 40° C. Seeds of Form C were added and the stirred mixture allowed to cool to room temperature. The product was collected by filtration, washed with anhydrous 2-butanone [20 ml] and dried in an oven at 100° C.

Weight of dried product 5.95 g

Melting point: 162°–163° C.

The infra-red spectrum (Nujol mull) was consistent with paroxetine hydrochloride anhydrate Form C.

EXAMPLE 18

Crystallization of paroxetine hydrochloride from toluene by seeding

Paroxetine hydrochloride anhydrate Form C [20.0 g] was dissolved in boiling toluene [200 ml] and approximately 50 ml of the solution added to each of 4 conical flasks. Each flask was heated again to boiling, allowing some toluene vapor to reflux out, in order to remove seeds. Flask 1 was immediately sealed with a ground glass stopper and set aside to cool. The remaining flasks were sealed with foil, and allowed to cool somewhat, before adding seed crystals as follows:

Flask 2 was seeded with paroxetine hydrochloride toluene solvate

Flask 3 was seeded with paroxetine hydrochloride anhydrate Form B

Flask 4 was seeded with paroxetine hydrochloride anhydrate Form C

The added seeds remained undissolved. The flasks were sealed with ground glass stoppers, stirred gently for a few seconds then set aside to cool. Flask 2 was observed to crystallize very readily, while in Flasks 3 and 4 crystallization took place more slowly. At this point Flask 1 remained completely clear, and all 4 flasks were left at room temperature overnight. The following morning Flask 1 contained only a few crystals, while Flasks 2, 3 and 4 had extensively crystallized.

Flask 1 was stirred gently for several hours, during which time the bulk of the paroxetine hydrochloride crystallized.

The product from each flask was collected by filtration and dried at 50° C. under vacuum.

| Flask 1 (not seeded) | |
| --- | --- |
| Weight of product: | 4.25 g |
| Appearance: | short needles/rods |
| Infra red spectrum: | consistent with paroxetine hydrochloride anhydrate |
| Form C | |
| Melting point: | 161–162° C. |
| Flask 2 (seeded with toluene solvate) | |
| Weight of product: | 3.80 g |
| Appearance: | long fine needles |
| Infra red spectrum: | consistent with paroxetine hydrochloride toluene solvate |
| Solvent content: | 11% wt/wt toluene by 1H-NMR |
| Melting point: resolidification and further | initial melt at about 70° C, followed by melt at 161–162° C. |
| Flask 3 (seeded with anhydrate Form B) | |
| Weight of product: | 4.20 g |
| Appearance: | needles |
| Infra red spectrum: | consistent with paroxetine hydrochloride anhydrate |
| Form B | |
| Solvent content: | 0.8% wt/wt toluene by 1H-NMR |
| Melting point: | 138–140° C. |
| Flask 4 (seeded with anhydrate Form C) | |
| Weight of product: | 4.93 g |
| Appearance: | needles |
| Infra red spectrum: | consistent with paroxetine hydrochloride anhydrate |
| Form C | |
| Solvent content: | 0.8% wt/wt toluene by 1H-NMR |
| Melting point: | 161–162° C. |

EXAMPLE 19

Crystalline Paroxetine Hydrochloride Anhydrate Substantially free of Bound Propan-2-ol (Form A)

Vacuum oven dried paroxetine hydrochloride propan-2-ol solvate containing 2.6% propan-2-ol (1 g) was placed in a glass tube. The tube was immersed in a water bath set at 50° C. and nitrogen gas, saturated with water vapor at a temperature of 40° C., was passed through the sample. After 10 hours a small sample was removed an analyzed by 1H-NMR, which showed that the level of propan-2-ol had fallen to 2.0%. The temperature of the bath surrounding the tube was increased to 80° C., and the temperature at which the gas being passed through the sample was saturated was increased to 70° C. After 10 hours the contents of the tube were sampled again and analyzed by 1H-NMR, which showed that the level of propan-2-ol had fallen further to 1.0%.

We claim:

1. Paroxetine hydrochloride anhydrate in Form C, which form comprises the following characteristics: a melting point of about 164° C.; IR bands at about 540, 574, 615, 674, 720, 760, 779, 802, 829, 840, 886, 935, 965, 984, 1007, 1034, 1092, 1109, 1139, 1183, 1218, 1240, 1263, 1280, 1507, 1540, 1558, 1598, and 1652 cm$^{-1}$; a DSC maximum exotherm measured at 10° C. per minute, of about 161° C. in both open and closed pans; characteristic X-ray diffractogram peaks at about 10.1, 12.1, 13.1, 14.3 degrees 2 theta; characteristic solid state $^{13}$C-NMR spectrum peaks at about 154.0, 148.5, 143.4, 140.4 ppm.

2. A pharmaceutical composition comprising paroxetine hydrochloride anhydrate in Form C and a pharmaceutically acceptable carrier, which Form C comprises the following characteristics: a melting point of about 164° C.; IR bands at about 540, 574, 615, 674, 720, 760, 779, 802, 829, 840, 886, 935, 965, 984, 1007, 1034, 1092, 1109, 1139, 1183, 1218, 1240, 1263, 1280, 1507, 1540, 1558, 1598, and 1652 cm$^{-1}$; a DSC maximum exotherm, measured at 10° C. per minute, of about 161° C. in both open and closed pans; characteristic X-ray diffractogram peaks at about 10.1, 12.1, 13.1, 14.3 degrees 2 theta, characteristic solid state $^{13}$C-NMR spectrum peaks at about 154.0, 148.5. 143.4, 140.4 ppm.

* * * * *